(12) United States Patent
Yeo et al.

(10) Patent No.: US 7,990,546 B2
(45) Date of Patent: Aug. 2, 2011

(54) HIGH THROUGHPUT ACROSS-WAFER-VARIATION MAPPING

(75) Inventors: Jeong Ho Yeo, Kyounggi-Do (KR); Efrat Rosenman, Asseret (IL); Erez Ravid, Jerusalem (IL); Doron Meshulach, Ramat-Gan (IL); Gadi Greenberg, Tel-Aviv (IL); Kobi Kan, Givatayim (IL); Yehuda Cohen, Rehovot (IL); Shimon Levi, Tivon (IL)

(73) Assignee: Applied Materials Israel, Ltd., Rehovot (IL)

( * ) Notice: Subject to any disclaimer, the term of this patent is extended or adjusted under 35 U.S.C. 154(b) by 281 days.

(21) Appl. No.: 12/173,766

(22) Filed: Jul. 15, 2008

(65) Prior Publication Data
US 2009/0021749 A1 Jan. 22, 2009

Related U.S. Application Data

(60) Provisional application No. 60/950,077, filed on Jul. 16, 2007.

(51) Int. Cl.
*G01B 11/24* (2006.01)
(52) U.S. Cl. .............. 356/601; 356/237.1; 356/237.5
(58) Field of Classification Search .... 356/237.1–237.5, 356/601, 636
See application file for complete search history.

(56) References Cited

U.S. PATENT DOCUMENTS

| | | | |
|---|---|---|---|
| 5,883,710 A * | 3/1999 | Nikoonahad et al. | 356/237.2 |
| 6,215,551 B1 * | 4/2001 | Nikoonahad et al. | 356/237.2 |
| 6,512,578 B1 | 1/2003 | Komatsu et al. | |
| 6,693,293 B2 | 2/2004 | Oomori et al. | |
| 6,809,808 B2 | 10/2004 | Feldman et al. | |
| 6,853,475 B2 | 2/2005 | Feldman et al. | |
| 6,862,491 B2 | 3/2005 | Levin et al. | |
| 6,891,627 B1 * | 5/2005 | Levy et al. | 356/625 |
| 7,027,145 B2 | 4/2006 | Segall et al. | |
| 7,239,389 B2 * | 7/2007 | Baer et al. | 356/369 |
| 7,248,354 B2 | 7/2007 | Kreh et al. | |
| 7,298,471 B2 | 11/2007 | Fukazawa et al. | |
| 7,369,224 B2 | 5/2008 | Oomori et al. | |
| 7,372,557 B2 | 5/2008 | Oomori et al. | |
| 2004/0125373 A1 * | 7/2004 | Oldenbourg et al. | 356/364 |
| 2004/0125375 A1 * | 7/2004 | Some | 356/369 |
| 2004/0239918 A1 | 12/2004 | Sugihara et al. | |

(Continued)

OTHER PUBLICATIONS

Oomori, Takeo et al, Novel inspection technology for half pitch 55 nm and below, Metrology, Inspection, and Process Control for Microlithography XIX, Proc. of SPIE vol. 5752, 2005, 9pp.

*Primary Examiner* — Tarifur R Chowdhury
*Assistant Examiner* — Isiaka O Akanbi
(74) *Attorney, Agent, or Firm* — SNR Denton US LLP (57) ABSTRACT

A method for characterizing a surface of a sample object, the method including dividing the surface into pixels which are characterized by a parameter variation, and defining blocks of the surface as respective groups of the pixels. The method further includes irradiating the pixels in multiple scans over the surface with radiation having different, respective types of polarization, and detecting returning radiation from the pixels in response to each of the scans. For each scan, respective block signatures of the blocks are constructed, in response to the returning radiation from the group of pixels in each block. Also for each scan, a block signature variation using the respective block signatures of the blocks is determined. In response to the block signature variation, one or more of the types of polarization for use in subsequent examination of a test object are selected.

19 Claims, 8 Drawing Sheets

U.S. PATENT DOCUMENTS

| | | |
|---|---|---|
| 2006/0098189 A1 | 5/2006 | Oomori et al. |
| 2006/0182335 A1 | 8/2006 | Levin et al. |
| 2006/0192953 A1 | 8/2006 | Fukazawa et al. |
| 2006/0232769 A1 | 10/2006 | Sugihara et al. |
| 2007/0046931 A1 | 3/2007 | Oomori et al. |
| 2008/0094628 A1 | 4/2008 | Fukazawa et al. |

* cited by examiner

HIGH THROUGHPUT ACROSS-WAFER-VARIATION MAPPING

CROSS-REFERENCE TO RELATED APPLICATION

This application claims the benefit of U.S. Provisional Patent Application 60/950,077, filed 16 Jul. 2007, which is incorporated herein by reference.

FIELD OF THE INVENTION

The present invention relates generally to quality inspection, and specifically to high throughput inspection.

BACKGROUND OF THE INVENTION

In a wafer fabrication facility, scanning using an optical system is one of the recognized methods for inspecting wafers for defects, irregularities, etc. The scanning approach irradiates all or a specific region of the wafer, for instance in a die or cell on the wafer, and measures one or more parameters of the returning radiation, which may be scattered, diffracted, and/or reflected radiation. The measured parameters may be compared with other respective, assumed "standard" parameters, typically in a cell-cell or die-die comparison, or in a comparison against previously determined values, to determine if the irradiated region is within specification.

The smallest features of elements of present day wafers typically have dimensions of the order of tens of nanometers. Systems for characterizing wafers at these orders of magnitude are known in the art, for example scanning electron microscopes (SEMs), scanning X-ray microscopes (SXMs), atomic force microscopes (AFMs), and Optical Critical Dimension (OCD) tools. However the scan rate of such systems is typically extremely low so that they are usually only used to characterize or inspect relatively small fractions of a wafer. If they are used on a whole 300 mm wafer, the procedure takes many hours or days.

The disclosure of U.S. Pat. No. 6,862,491 to Levin et al., is incorporated herein by reference. Its Abstract states: "A method to extend the process monitoring capabilities of a semiconductor wafer optical inspection system so as to be able to detect low-resolution effects of process variations over the surface of a wafer at much higher sensitivity than heretofore possible."

A paper titled "Novel inspection technology for half pitch 55 nm and below" by Omori et al, in Metrology, Inspection, and Process Control for Microlithography XIX, edited by Richard M. Silver, in Proc. of SPIE Vol. 5752, 2005 is incorporated herein by reference. The paper relates to a system for inspecting surfaces.

The following U.S. patents and patent applications, all of which are incorporated herein by reference, relate to systems for inspecting surfaces: U.S. Pat. Nos. 6,512,578, 6,693,293, 7,027,145, 7,248,354, 7,298,471, 7,369,224, 7,372,557, 2004/0239918, 2006/0098189, 2006/0192953, 2006/0232769, 2007/0046931, 2008/0094628.

However, notwithstanding the systems at present available, an improved method for inspecting surfaces is desirable.

SUMMARY OF THE INVENTION

In an embodiment of the present invention, an optimum type of polarized radiation to be used to examine a surface of objects, typically wafers such as production wafers, is determined. The radiation may comprise linear, circular, or elliptical polarized radiation. Typically, different regions of the surface, including regions having periodic structures, reflect the polarized radiation differently according to the type of polarized radiation used.

In one embodiment a physical reference wafer is first characterized, typically by measuring a parameter-under-investigation, such as a line width, with a system such as a scanning electron microscope (SEM), so generating reference measurements of the parameter-under-investigation. The reference wafer is then scanned with different types of polarized radiation, each respective scan comprising focusing a spot onto the surface and scanning the spot across the surface. The spot defines a size of pixels into which the surface is divided. Typically there are 3-4 pixels per spot, but other numbers of pixels are possible. The different types of polarized radiation comprise differently oriented linearly polarized radiation, left and right circularly polarized radiation, and left and right elliptically polarized radiation having different eccentricities. A processor stores bright field, and/or gray field, and/or dark field returning radiation measurements from pixels on the surface of the reference wafer. The processor groups the pixels into blocks, typically rectangular blocks having sides of the order of 50 pixels, and calculates a respective block signature for each of the blocks.

In a disclosed embodiment a block signature is a function of the returning radiation measurements of all the pixels in the block for one given type of polarized radiation. For example, a block signature may be an arithmetic mean of the bright field measurements of all the pixels for left circularly polarized radiation. The processor compares block signatures produced by the different types of polarized radiation with the reference measurements. From the comparisons, the processor selects the type of polarized radiation that produces the highest block signature change for the changes of the reference measurements, i.e., the type of polarized radiation for which the block signatures have a maximum sensitivity to changes in the reference measurements. The processor uses the selected type in examining or scanning test objects, such as production, calibration, or research and development wafers, and uses the function to generate block signatures of the objects. The block signatures may characterize the objects in the same manner, and with generally the same resolution, as the reference measurements, but a scan to produce the block signatures takes a fraction of the time required to form the reference measurements for the objects.

In an alternative embodiment, a composite block signature is a generated function of the returning radiation measurements of all the pixels in the block for two or more different types of polarized radiation. For example, a composite block signature may be formed from a linear combination of a first multiple of the bright field (or gray field) measurement for a first linear polarization and a second multiple of the bright field (or gray field) measurement of a linear polarization that is orthogonal to the first polarization, the linear combination being summed over all the pixels in the block to form the composite block signature. In general, a composite block signature may be a function formed from the different types of polarization and their bright field, gray field and/or dark field measurements. The processor compares different composite block signatures with the reference measurements. From the comparisons, the processor selects the composite block signature change that has maximum sensitivity to changes of the reference measurements. To examine objects, the processor uses data from scans of the objects with the types of polarized radiation required for the function that generates the selected composite block signature, and generates composite block signatures of the objects using the function.

In a further alternative embodiment, rather than using data from a physical reference wafer, the processor uses data from simulations and other sources to set characteristics of a simulated reference wafer. The processor performs substantially similar operations to those described above for the physical reference wafer, for example, simulating irradiating the simulated wafer with different types of polarized radiation. From the results of the simulation, the processor is able to determine one or more types of polarized radiation with which to irradiate physical test objects.

The present invention will be more fully understood from the following detailed description of the embodiments thereof, taken together with the drawings, a brief description of which follows.

DETAILED DESCRIPTION OF EMBODIMENTS

Figure 1:
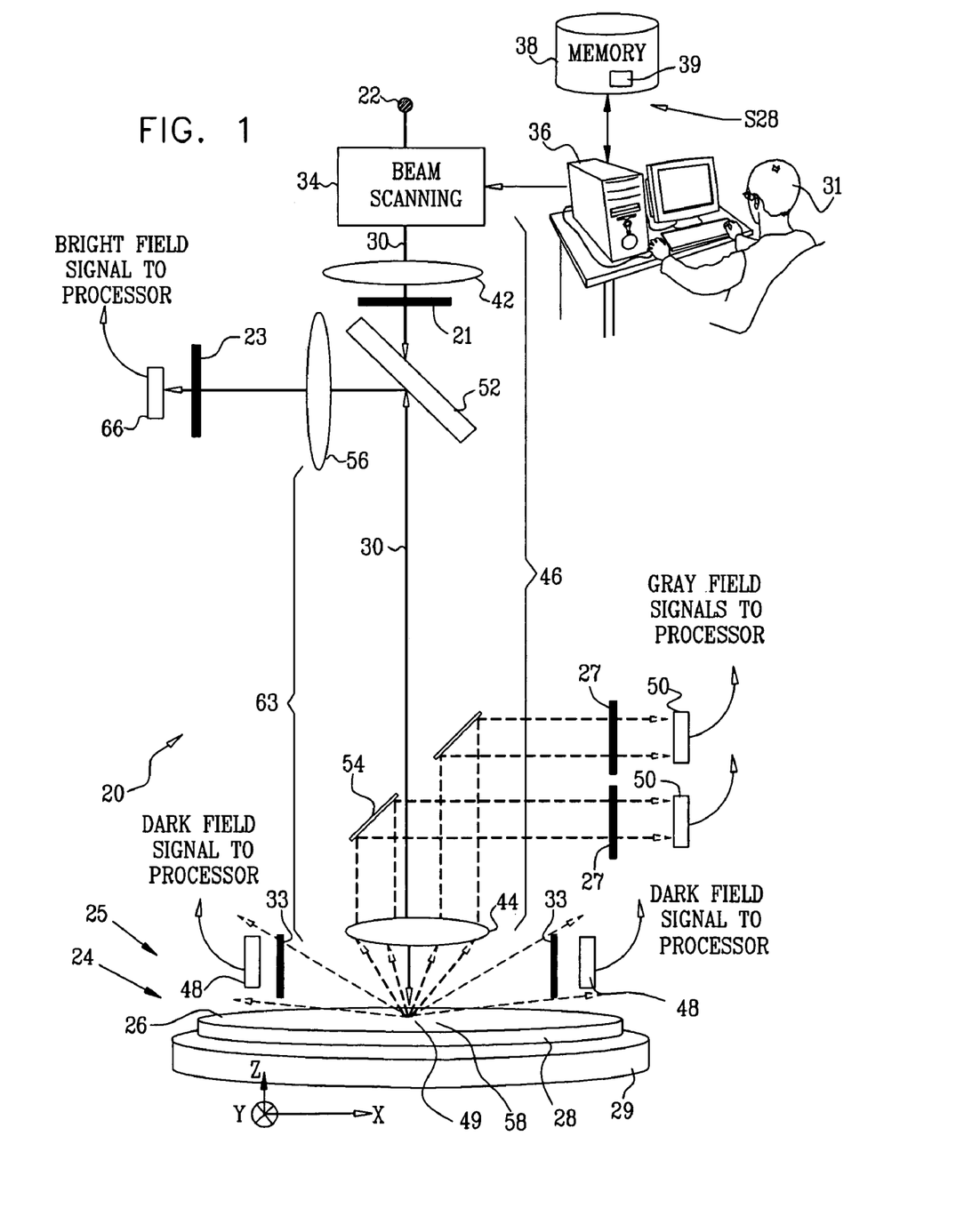
FIG. 1 is a schematic diagram of a surface examination apparatus, according to an embodiment of the present invention.

Reference is now made to FIG. 1, which is a schematic diagram of a surface examination apparatus 20, according to an embodiment of the present invention. Apparatus 20 acts as a radiation scanner of surfaces of a sample object and test objects, which are typically a reference wafer and production wafers. The apparatus comprises a source 22 of radiation which generates a beam 30 that is used to irradiate a surface 26. Herein, by way of example, surface 26 is assumed to comprise the surface of a wafer 28, but it will be appreciated that embodiments of the present invention may be used for irradiation and/or examination of substantially any surface. Wafer 28 typically has a multiplicity of substantially similar dies 24 formed on its surface. There are a multiplicity of functional features 25, such as memory cells, logic cells, or groups or components thereof, within each die. In the following description, specific dies 24 are distinguished from each other by adding a letter suffix to the identifying die numeral, for example die 24A. In addition, specific wafers or types of wafers 28, such as production wafers, or wafers used for calibration, are distinguished by adding a letter suffix to the identifying wafer numeral, for example production wafer 28P and calibration wafer 28C. Source 22 is typically a laser, although any other suitable source of radiation, such as a suitable ultra-violet (UV) or deep UV (DUV) source, may be used to generate beam 30. An operator 31 may control apparatus 20, or alternatively the apparatus may be configured to operate completely automatically.

Embodiments of the present invention may also use a computer simulated wafer. In the description herein, a simulated wafer is distinguished from a physical wafer by having a letter prefix added to the identifying wafer numeral of the simulated wafer, for example simulated wafer S28. Computer simulated wafers are typically stored as software instructions and/or data in a memory 38.

For clarity in the following description, surface 26 is assumed to define an x-y plane, with the x-axis lying in the plane of the paper, and the y-axis going into the paper. A z-axis is normal to the x-y plane, as shown in FIG. 1. The description also uses, for clarity, positional terms with respect to the figures such as left side and lower section of the wafer. The axes and the positional terms are arbitrary, and are not to be construed as limiting the scope of the present invention.

By way of example, beam 30 is assumed to enter a beam scanning module 34 which scans the beam in an x-direction, typically using rotating mirrors and/or acousto-optic deflectors. Module 34 is part of a set of projection optics elements 46. Systems for performing the functions of module 34 are well known in the art. U.S. Pat. Nos. 6,853,475 and 6,809,808 to Feldman et al, describe examples of such systems, and are incorporated herein by reference. Module 34 is controlled by a processor 36, which also operates other elements of apparatus 20. Alternatively, module 34 is not present in projection optics elements 46, in which case apparatus 20 may be arranged in an area imaging configuration wherein beam 30 illuminates an area of surface 26. In this configuration, surface 26 may be scanned by moving the wafer. In both systems, pixel sizes, described in more detail below, are substantially the same. Those having ordinary skill in the art will be able to adapt the description herein, mutatis mutandis, for an area configuration.

Processor 36 is coupled to memory 38, wherein are stored software instructions 39 for operation of the apparatus. Instructions 39 can be supplied to apparatus 20 as a computer software product, in electronic form or on tangible media such as a magnetic storage disc or a compact disc which are readable by a computer, or by other means known in the art for permanent storage of electronic data.

Projection optics elements 46 includes one or more polarizing elements 21 which change the polarization of beam 30 under control of processor 36. Beam 30 is typically polarized, in which case elements 21, herein also termed polarizer 21, may comprise a half- or a quarter-wave plate, or a combination of these plates, which receives beam 30 and which alters the characteristic of the beam exiting polarizer 21. Processor 36 is able to rotate the axis of the half- or quarter-wave plate so as to define the characteristic of the beam exiting the plate. If beam 30 is not polarized, elements 21 typically comprise a linear polarizer, which may be followed by a half- or quarter-wave plate.

Thus, polarizer 21 may convert beam 30 into one of three modes of polarized radiation: linearly, circularly, or elliptically polarized radiation, where the eccentricity e of the elliptically polarized radiation is in the range $0<e<1$. Processor 36 is able to select the mode of polarization for a particular scan, and is also able to define parameters of the mode. The parameters that the processor defines are dependent on the mode: for the linearly polarized mode, the parameter is the direction of polarization; for the circularly polarized mode the parameter sets if the polarization is left or right circularly polarized radiation; and for the elliptically polarized mode the parameter sets the ellipticity e of the polarized radiation, as well as whether the exiting radiation is left or right elliptically polarized. The combination of a mode of polarization, and of the parameter applying to the mode, is hereinbelow referred to as the type of polarization. For example, one type of polarization is radiation that is linearly polarized along a y-axis, wherein the mode is linear and the parameter of the mode is the y-axis direction.

Elements 46 also include other elements, indicated schematically in FIG. 1 by a relay lens 42 and an objective lens 44. Projection optics 46 function to project and focus radiation from beam 30 onto a spot 49 on surface 26. Optics 46 also include a beamsplitter 52, which allows transmission of beam 30 to surface 26.

Typically, spot 49 covers a small region of surface 26, and the size of the region typically governs the sizes of rectangular pixels 58 into which the surface is assumed to be divided. The size of spot 49, and thus of a pixel, is a function of several factors including the wavelength of source 22 and the numerical aperture of the optics. The pixel size is typically selected according to the design rule used in forming dies 24 on the surface. For example, each pixel 58 may be a square having a side in a range of 80-160 nm. While pixels 58 taken together may tile, i.e., completely cover, surface 26, this is not to be construed that apparatus 20 necessarily scans the entire surface, since in some embodiments only selected regions of the surface may be scanned.

Wafer 28 is mounted on a motion stage 29 which is controlled by processor 36. Stage 29 rotates and translates the wafer, as well as bringing the wafer into focus, using independent x-, y-, and z-translation stages, as well as one or more rotation stages. Processor 36 controls the movement of the motion stages, as well as the scanning performed by module 34, so that substantially any part of surface 26 may be irradiated by beam 30. The particular motions generated by module 34 and stage 29 are described in more detail below.

Returning radiation from spot 49 is typically of three forms: bright field radiation, comprising radiation which is substantially specularly reflected from surface 26, dark field radiation, which is typically radiation which is scattered from surface 26 at relatively large angles to the path of the specular reflected radiation, and gray field radiation, which is scattered from surface 26 at angles generally between the path of the specular reflected radiation and the dark field radiation. Generally, in examining surface 26, all three forms of returning radiation may be measured.

In apparatus 20 beam 30 is arranged to be incident substantially normally on surface 26, although the apparatus could be set to operate at non-normal angles of incidence. A mirror 54 has a hole at its center to allow free passage of beam 30, as well as returning specular radiation from spot 49. Specular radiation from spot 49 traverses objective 44, and is reflected by beamsplitter 52 via a lens 56 to a bright field detector 66. In some embodiments a polarizing analyzer 23 precedes detector 66. Objective 44, beamsplitter 52, and lens 56 are part of a set of receiving optics 63.

Mirror 54 reflects gray field radiation from spot 49 to one or more gray field detectors 50. Detectors 48 measure the incoming dark field radiation. In some embodiments polarizing analyzers 27 and 33 respectively precede respective gray field detectors and dark field detectors. For simplicity, in FIG. 1 a section of one annular gray field detector, and two dark field detectors are shown, but any suitable number of each type may be used in apparatus 20. Typically, the dark field and gray field detectors are effectively distributed approximately symmetrically about beam 30. By way of example, apparatus 20 is assumed to comprise a total of 6 bright field, gray field, and dark field detectors.

Modes and/or parameters of analyzers 23, 27, and 33, if present, are set by processor 36, typically to correspond with the mode and parameter of polarizer 21.

Returning radiation from spot 49 impinges on each of detectors, 66, 50, and 48, and the detectors in turn generate respective signal levels for each pixel 58 according to their received radiation intensity. The specific signal levels for each detector are characteristic of the functional and/or structural features of the pixel being irradiated, as well as of the intensity and direction of polarization of beam 30. Thus, a matrix formed from up to 6 different detector levels, or received radiation intensity levels, may be associated with each pixel 58, element values of the matrix for a particular pixel being dependent on the functional/structural features of the pixel. For example, a pixel which comprises a conducting material line, such as is commonly used in semiconductor wafers, typically has a significantly different matrix compared to the matrix associated with an insulator.

As is described above, apparatus 20 may monitor bright field, gray field, and dark field returning radiation. Alternatively, apparatus 20 may not monitor all of these returning radiations. Except where otherwise stated, for simplicity the following description assumes that only signals from returning bright field radiation are used, so that only detector 66 is operative. Those having ordinary skill in the art will be able to adapt the description, mutatis mutandis, for embodiments wherein signals from bright, gray, and/or dark fields are used.

Typically, processor 36 examines surface 26 as quickly as possible. The processor typically performs the examination by irradiating consecutive pixels of the surface, each pixel being examined by scanning beam 30 in the x-direction while translating surface 26 in the y-direction. To reduce the time spent on examination, processor 36 may set the rate of scanning of beam 30 and the rate of translation of surface 26 as high as possible, while providing an acceptable signal to noise level at detector 66, and while maintaining an acceptable number of pixels per spot 49. Typically, rates of mechanical scanning across surface 26 are in the range 80-260 mm/s.

By way of example, the description herein assumes that apparatus 20 uses one beam 30 which irradiates a single spot 49 of surface 26. Methods are known in the art to irradiate multiple spots of surface 26 substantially simultaneously, for example, by multiplexing beam 30 into a multiplicity of beams, and/or by using multiple radiation sources. Those having ordinary skill in the art will be able to adapt the description herein, mutatis mutandis, for systems irradiating multiple spots and deriving measurements of respective regions of an irradiated surface substantially simultaneously.

Figure 2:
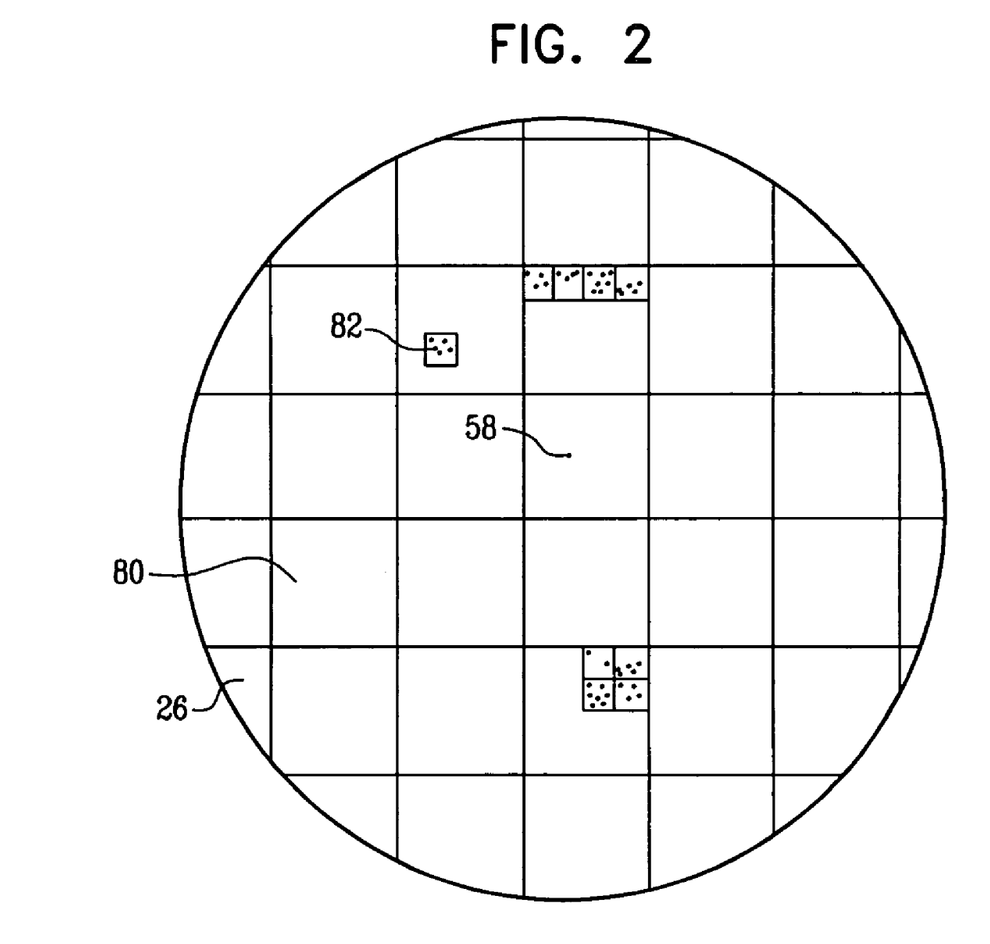
FIG. 2 is a schematic diagram of a surface, according to an embodiment of the present invention.

FIG. 2 is a schematic diagram of surface 26, according to an embodiment of the present invention. The surface is assumed to be divided into substantially congruent dies 80, and each of the dies is typically eventually used as part of an electronic device such as a memory. Using an exemplary pixel dimension of 100 nm, within the range exemplified above, for a die that is a square having side 1 mm, each die comprises 10,000×10,000 pixels. By way of example, dies and the pixels comprising the dies are assumed to be arranged as Cartesian arrays, so that any specific die or any specific pixel may be uniquely identified by an x-coordinate and a y-coordinate.

In embodiments of the present invention, relatively large numbers of pixels are grouped into equal-size blocks 82. For a grouping of 50×50 pixels forming blocks 82, each die 80 of side 1 mm is formed of 200×200 blocks. In one embodiment block 82 is a group of 32×32 pixels. However, it will be understood that each block 82 may comprise any convenient number of pixels. It will also be understood that although block 82 is typically rectangular, there is no requirement that this condition be satisfied, so that the block may be formed as any convenient closed figure of contiguous pixels.

A block signature is determined for any specific block 82. Each block signature is formed from a histogram of measured values of the pixels of the block. The histogram may be one-dimensional (1D), for example plotting frequencies of intensities of bright field returning radiation from the pixels of the block. Alternatively, the histogram may be two-dimensional (2D), for example plotting frequencies of ordered pairs (intensity, intensity spread of neighboring pixels) of bright field returning radiation from the pixels of the block.

Further alternatively, in general the histogram for a block signature may be n-dimensional (nD), where n is a natural number, plotting frequencies of ordered n-tuples $(x_1, x_2, x_3, \ldots x_n)$ where $x_1 \ldots$ are parameters of a pixel measurement. An example of a four-dimensional histogram that may be used for a block signature plots frequencies of the 4-tuple $(I_b, S_b, V_b, I_g)$, where $I_b$ is the returning bright field radiation intensity from a specific pixel in the block, $S_b$ is the spread of returning bright field radiation intensities for nearest neighbors of the specific pixel, $V_b$ is the variation of $S_b$, and $I_g$ is the returning gray field intensity from the specific pixel.

The block signature is a number representative of the values of the histogram. For example, for a 1D histogram a percentage of the distribution, an arithmetic mean, or a median of the histogram values may be calculated, and the percentage, the mean or the median used as the block signature.

In an embodiment of the present invention, a block signature is determined for a specific type of polarization of the radiation incident on surface 26. As is described in more detail below, the specific type of polarization is typically determined by constructing block signatures for different polarization types, and determining the type that gives an optimal signature for a parameter or parameters being investigated, initially by examination of a calibration wafer.

Figure 3:
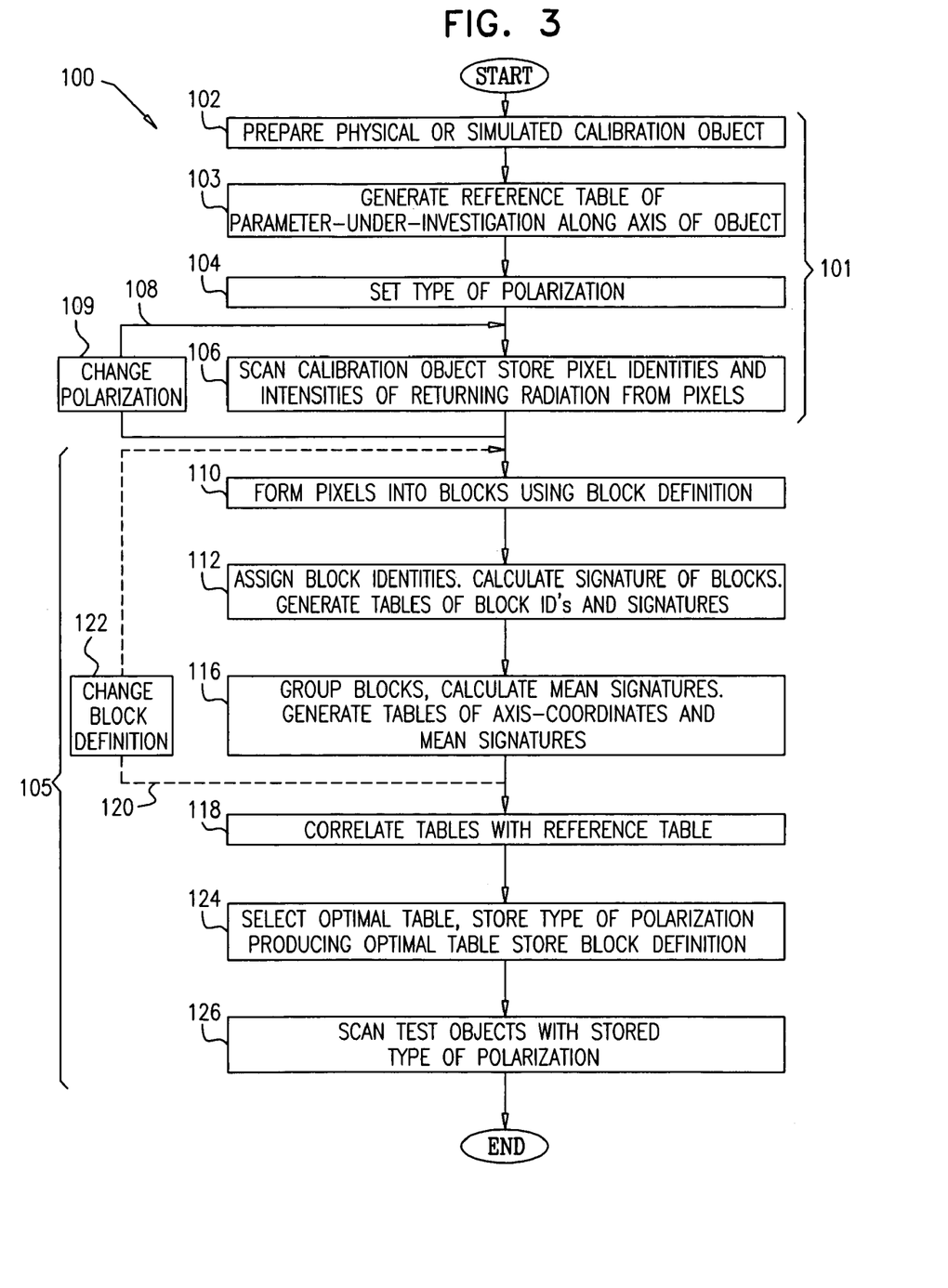
FIG. 3 is a flowchart describing a process to determine a type of polarization to be used in investigating a production wafer, according to an embodiment of the present invention.
Figure 4:
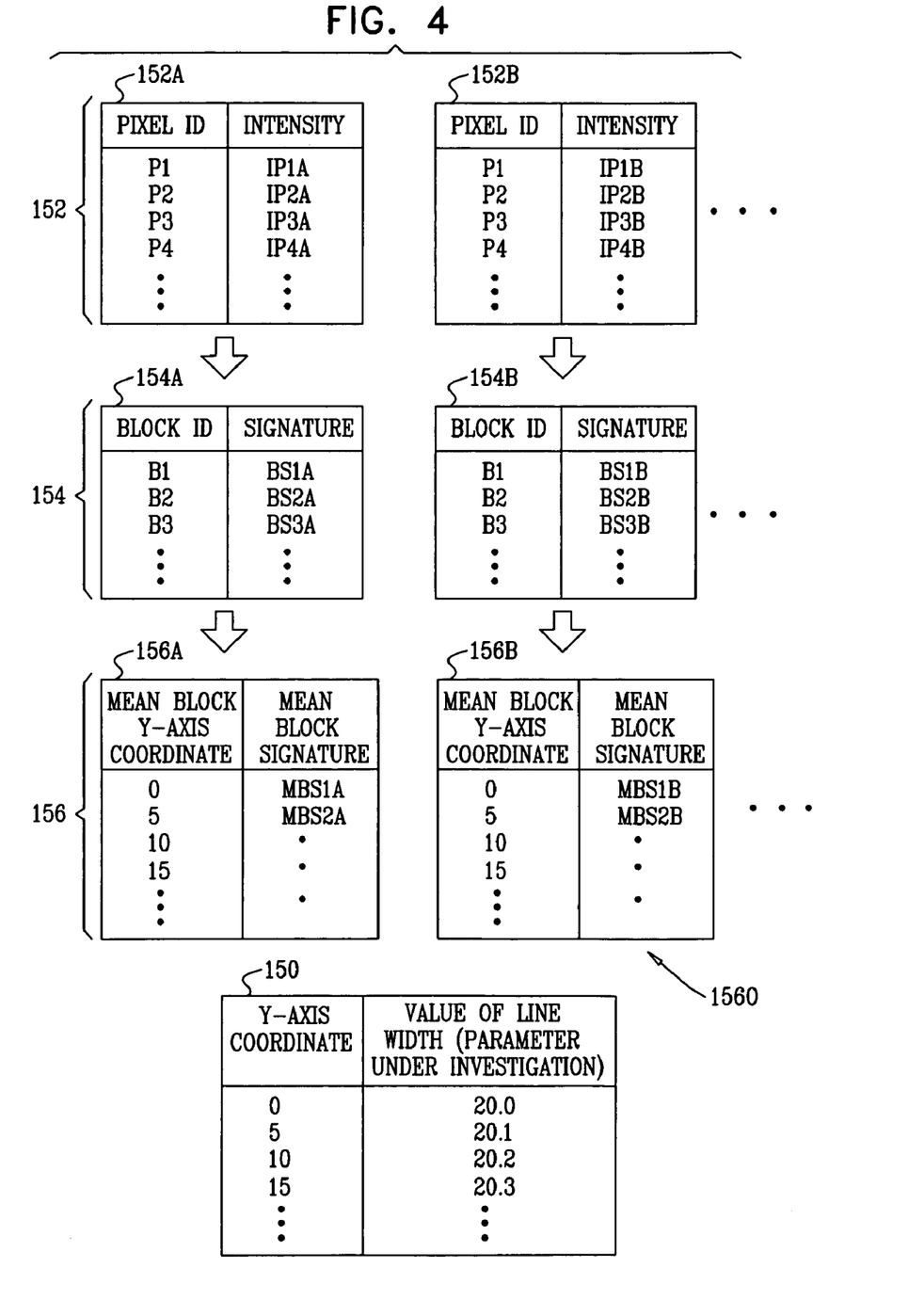
FIG. 4 shows tables formed by a processor in performing the process of FIG. 3, according to embodiments of the present invention.

FIG. 3 is a flowchart 100 describing a process to determine a type of polarization to be used in investigating a production wafer, and FIG. 4 shows tables formed by processor 36 in performing the process, according to embodiments of the present invention. The process described by flowchart 100 is assumed to be performed by processor 36 using instructions 39, and is to find a type of polarized radiation with which any object to be tested is scanned. Hereinbelow, by way of example, objects to be tested are assumed to be production wafers 28P.

There are two sections to the process described by flowchart 100: a first, results generation section 101, and a second, analysis section 105.

In section 101, in a preparation step 102, a calibration object is prepared. The calibration object may comprise a calibration wafer, a production wafer having a calibration region in the production wafer, or any other suitable object that provides a known variation of the parameter or parameters that are to be measured. Hereinbelow, by way of example the calibration object is assumed to comprise a calibration wafer 28C which is physically fabricated. In some embodiments, a focus exposure matrix (FEM) wafer is used as calibration wafer 28C. As is known in the art, an FEM wafer comprises a wafer in which a reticle exposes a mask with multiple combinations of focus and exposure settings onto the wafer that has been coated with a photoresist. The FEM wafer is characterized, typically with a CD-SEM (critical dimension scanning electron microscope) to determine resist profiles and line widths, and the corresponding focus and exposure settings, that most closely match a desired profile and line width. Alternatively, parameters of the calibration object are simulated.

In the description of flowchart 100, preparation step 102 is assumed to comprise physical fabrication of calibration wafer 28C, and those having ordinary skill in the art will be able to adapt the description, mutatis mutandis, to the case where parameters of the calibration wafer are simulated.

In the following description, except where otherwise stated, the calibration wafer is assumed to be formed to have a known variation of the parameter or parameters that are to be measured, also herein termed the parameter- or parameters-under-investigation, across production wafers 28P. For the calibration wafer, typical parameters formed with a known variation include, but are not limited to, line width, line height, and line spacing. Those having ordinary skill will be aware of other parameters, such as line edge roughness, surface roughness, sidewall angle, composition, or amount of doping, that may vary across a wafer, and all these parameters are included in the scope of the present invention.

By way of example, in the description of flowchart 100 herewith, one parameter is assumed to be measured, and the parameter is assumed to be a line width. (Flowchart 300, below, describes a process wherein more than one parameter is measured.) An acceptable range for the line widths of production wafers 28P is typically approximately +/−5% from a nominal value. Wafer 28C is fabricated so that the line widths vary within this range, and so that the variation is substantially linear along one of the axes of the wafer. The axis of variation is assumed to correspond to the y-axis of the wafer.

In a reference step 103 processor 36 generates a reference calibration table 150 (FIG. 4) of the line width as it varies along the y-axis of the wafer, the table comprising one-to-one correspondences of y-coordinates of the wafer and line widths at the y-coordinate. By way of example, the line width of the conductors is assumed to be determined by processor 36 scanning different regions of wafer 28C using a scanning electron microscope (SEM). The processor then calculates the line widths for different values of y from the scanned results, to produce table 150, and the processor stores values of the table in memory 38 for use later in the process described by flowchart 100. Although the varying parameter is assumed herein to be measured using an SEM, processor 36 may use any convenient system known in the art, for example Optical Critical Dimension (OCD) metrology or a scanning X-ray microscope (SXM), to generate reference calibration table 150.

In a set polarization type step 104, processor 36 adjusts elements of apparatus 20 so that the y-axis of calibration wafer 28C corresponds to the y-axis of the apparatus. By way of example, polarizer 21 is hereinbelow assumed to be set to generate linear polarization, and processor 36 also sets the direction of the linear polarization. If present, analyzers 23, 27, and/or 33 are also set to transmit linear polarized radiation, and the direction of transmission is set to correspond to the direction set for polarizer 21. Alternatively, the type of polarization set in step 104 may comprise circular or elliptical polarization.

In a scan step 106, processor 36 scans calibration wafer 28C. The processor stores the intensity measured at bright field detector 66, for each pixel of the calibration wafer in memory 38, in the form of a pixel table 152A of pixel identifiers (IDs), determined from the x-coordinate y-coordinate of each pixel, and intensities of the corresponding pixels. Table 152A thus comprises one-to-one correspondences of unique pixel IDs P1, P2, . . . and intensities IP1A, IP2A, . . . of the identified pixel. In other embodiments, the intensities measured at gray field detectors 50 and/or dark field detectors 48 are also stored and incorporated into table 152A.

As indicated by a line 108, processor 36 repeats steps 104 and 106 for different types of polarization, the number of different types typically being controlled by operator 31. The type of polarization is changed in a change polarization step 109. In the case of linear polarization, the types include at least two different orthogonal polarizations. Thus, in step 106, there are a respective number of tables 152A, 152B, . . . formed, the number corresponding to the number of different types of polarization implemented in steps 104 and 106, each of the tables having the same one-to-one correspondence format as table 152A. Tables 152A, 152B, . . . are herein also referred to generically as tables 152.

Results generation section 101 completes when a final scan step 106 has been performed. The following steps of flowchart 100 comprise results analysis section 105.

In a block formation step 110, processor 36 selects groups of contiguous pixels that are to be considered as respective blocks. The selection may be performed on a completely automatic basis, for example by operator 31 defining a size of a rectangular block before the process of flowchart is begun. Alternatively, the operator may, for example on an iterative basis, set different sizes for the group of pixels to be considered as a block. Although blocks are typically selected to be rectangular, this is not a requirement, so that blocks having non-rectangular shapes may also be defined.

In a block signature step 112, for each type of polarization scanned in step 106, processor 36 calculates the block signature BS1, BS2, . . . of each block of pixels, using the intensities stored in tables 152. In addition, processor 36 assigns a unique block ID, B1, B2, . . . derived from a block's x- and y-coordinates, to each block. The processor uses tables 152 to find intensities of pixels within each of the blocks. By way of example, a block signature of a given block is calculated as the arithmetic mean of the intensities of the pixels in the given block. In general, a given block signature BSn (n a natural number) is a function of the intensities of the pixels in block Bn. Processor 36 generates from tables 152A, 152B, . . . respective tables 154A, 154B, . . . , each table 154A, 154B, . . . having a one-to-one correspondence of block IDs and block signatures, BSnA, BSnB, . . . . Tables 154A, 154B, . . . are also referred to generically herein as tables 154.

In a first analysis step 116, processor 36 groups the blocks according to the axis of variation of the parameter being measured, in this case according to the y-coordinates of the blocks. The processor then calculates the mean block signature for each group of blocks having the same y-coordinates, and forms as respective tables 156A, 156B, one-to-one correspondences of y-coordinates and mean block signatures MBS1A, MBS2A, . . . MBS1B, MBS2B, . . . at the y-coordinates. Tables 156A, 156B, . . . are also referred to generically herein as tables 156.

In some embodiments of the present invention, processor 36 reiterates steps 110 to 116 using a different definition for a block, the different definition typically comprising a change in rectangular dimensions of the block. Alternatively or additionally, the different definition of a block may comprise a change in shape of the block. The reiteration is illustrated in flowchart 100 by a broken line 120, and a change block definition step 122.

In a second analysis step 118, processor 36 correlates the mean block signatures of each of tables 156 with the line widths of the corresponding y-coordinates, as stored in table 150. The processor uses the correlation to determine which table of mean block signatures gives the highest variation of block signatures for the variation of line widths. In other words, the processor determines a maximum sensitivity of the block signatures for the changes in line width. Typically, for every table 156A, 156B, . . . processor 36 performs a linear regression analysis of the mean block signatures with the parameter-under-investigation of table 150, and determines from the regression analysis a variation of block signatures corresponding to the variation of line widths, as well as a correlation coefficient, for each table 156A, 156B, . . . .

In a selection step 124, the processor determines which table 156A, 156B, . . . herein termed an optimal table 156O, gives the maximum sensitivity of the block signatures. The processor stores the type of polarization used to generate optimal table 156O in memory 38. The processor also stores the block definition used to generate optimal table 156O in memory 38.

In a final step 126, the processor scans production wafers 28P with the type of polarization determined in selection step 124, substantially as described for steps 104 and 108 above. From the scan results processor 36 determines block signatures of blocks in wafers 28P, typically using the block definition of step 124 and the method for determining block signatures used in step 112. In some embodiments the block definition used for production wafers 28P is altered, typically so as to improve a signal to noise ratio of the block signatures. Operator 31 uses the block signatures determined in step 126 to estimate variations in the parameter-under-investigation across the production wafers 28P.

Flowchart 100 then ends.

In some embodiments, as well as (as described in step 102 of flowchart 100) forming the parameter of the calibration wafer to have a known variation, a wafer may be formed so that the parameter-under-investigation does not vary over the wafer. In this case, in addition to finding the type of polarization giving the maximum sensitivity for the block signature variations using the wafer with the known variation, the type of polarization and block definition found for the varying parameter may be tuned to give block signatures that do not vary using the wafer with the non-varying parameter. Those having ordinary skill in the art will be able to adapt the description of flowchart 100 above, mutatis mutandis, to determine an optimal type of polarization giving block signatures which do not vary, by, for example, in steps 110 and 122 finding a block definition, in step 118 finding correlation coefficients, and in step 124 finding the type of polarization giving the highest correlation coefficient.

Wafer measurements using systems such as a CD-SEM are extremely time-consuming, and consequently costly, although the measurements have a high characteristic resolution. Measuring a small region of one wafer typically takes of the order of 10 minutes. If a complete wafer is measured with a CD-SEM, the time is many hours, if not days. The inventors have found that results from the process of flowchart 100 may be as good as those produced by wafer measurement system such as a CD-SEM, although apparatus 20 typically has a resolution one or more orders of magnitude less than the characteristic resolution of systems such as the CD-SEM. Furthermore, the process of flowchart 100 is significantly less time-consuming than that of the CD-SEM system, and this is particularly true if, as is required for production wafers, the whole wafer is to be measured. The inventors have found that a complete production wafer may be satisfactorily scanned, giving block signatures with good signal to noise ratios, typically in less than one hour. Moreover, the process of flowchart 100 may be combined with other optical scanning measurements performed by apparatus 20, such as die-to-die comparisons, simultaneously. Thus, the results of a single optical scan of a production wafer, typically taking less than one hour, may be used to generate block signatures of all blocks of the wafer, as described in step 126, as well as to perform die-to-die comparisons. The overall savings in time in measuring production wafers are consequently considerable.

Figure 5:
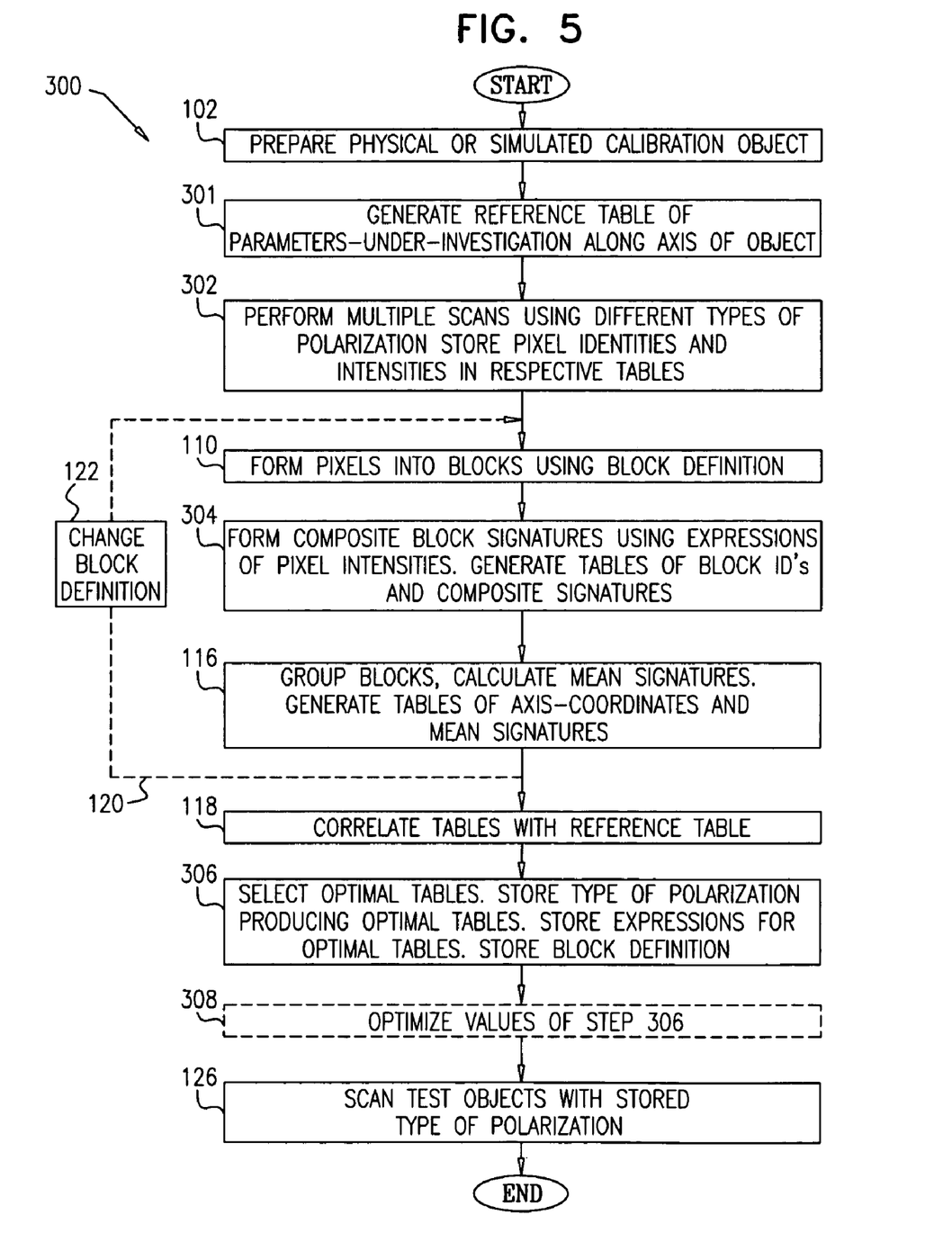
FIG. 5 is a flowchart describing a process to determine one or more functions of types of polarization to be used in investigating a production wafer, according to embodiments of the present invention.
Figure 6:
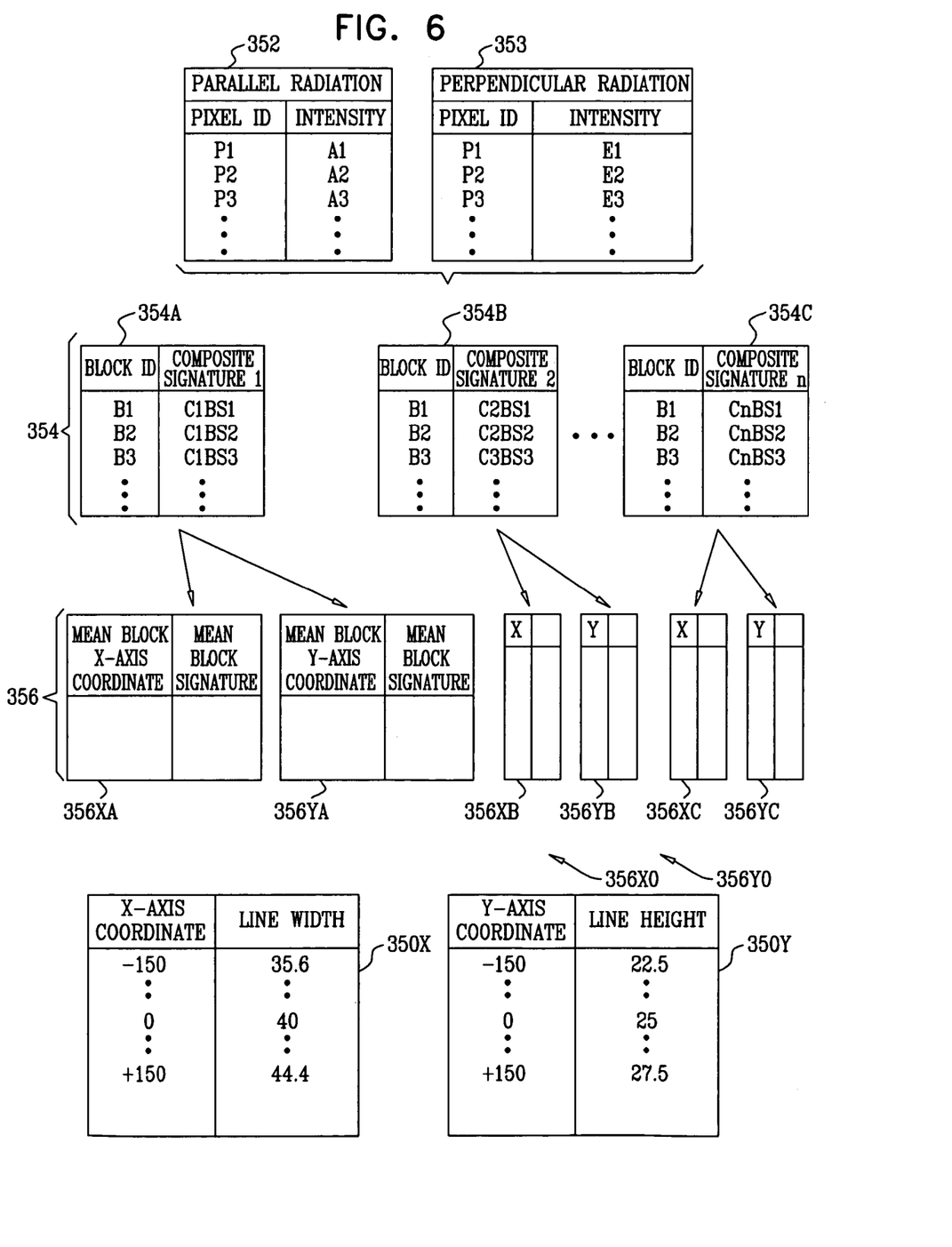
FIG. 6 shows tables formed by the processor in performing the process of FIG. 5, according to embodiments of the present invention.

FIG. 5 is a flowchart 300 describing a process to determine one or more functions of types of polarization to be used in investigating a production wafer, and FIG. 6 shows tables formed by processor 36 in performing the process, according to embodiments of the present invention. Apart from the differences described below, the process described by flowchart 300 is generally similar to the process of flowchart 100 (FIGS. 3 and 4) and operations performed in steps indicated by the same reference numerals in both flowchart 100 and flowchart 300 are generally similar.

Figure 7:
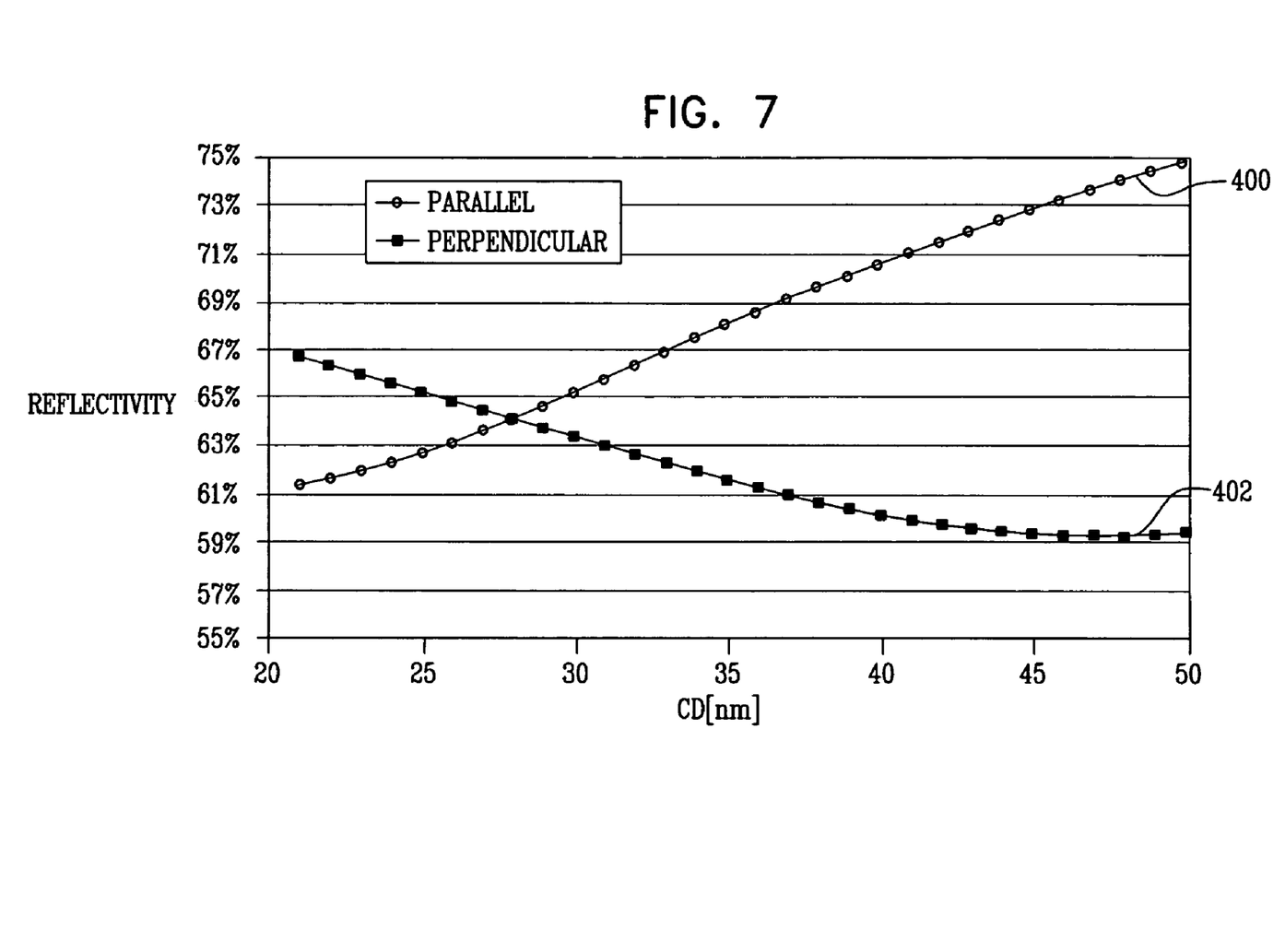
FIG. 7 shows graphs of reflectivity vs. line width, for two modes of linearly polarized radiation, according to an embodiment of the present invention.

FIG. 7 shows two graphs 400 and 402 of reflectivity vs. line width, for two modes of linearly polarized radiation, according to an embodiment of the present invention. Graphs 400 and 402 are prepared by simulation. Both graphs plot reflectivity vs. line width, the line widths being widths of a set of parallel lines where the line plus space is constant, giving a constant pitch. Graph 400 shows the reflectivity for a first mode of linearly polarized radiation that is parallel to the set of parallel lines. Graph 402 show the reflectivity for a second mode of linearly polarized radiation that is perpendicular to the set of parallel lines. Simulated results such as those illustrated by graphs 400 and 402 are used in the process of flowchart 300.

Returning to FIG. 5, the process described by flowchart 300 is assumed to be performed by processor 36 using instructions 39. The process finds multiple types of polarization with which production wafers 28P are to be scanned, and determines expressions having the multiple types of polarization that are to be used in generating block signatures of the wafers.

In preparation step 102 a simulated calibration wafer S28C is generated. By way of example, wafer S28C is assumed to have a linear variation along the x-axis of a line width, and a linear variation along the y-axis of a line height.

In a reference step 301, which is generally similar to reference step 103, the line width variation is set at +/−11% from a nominal line width. The line height variation is set at +/−10% from a nominal line height. Processor 36 produces two reference calibration tables 350X and 350Y, table 350X having a correspondence between the x-coordinate of the wafer and the line width, table 350Y having a correspondence between the y-coordinate of the wafer and the line height (FIG. 5).

A simulated scan step 302 replaces steps 104, 108, and 109 of flowchart 100. In step 302 processor 36 performs multiple simulated scans of wafer S28C, each scan using a different type of polarization. Hereinbelow the multiple types of polarization are assumed, by way of example, to consist of a first scan of linearly polarized radiation with the direction of polarization being parallel to the set of lines in wafer S28C, and a second scan of linearly polarized radiation with the direction of polarization being perpendicular to the set of lines in the simulated wafer. The two scans generate tables 352 and 353, respectively for parallel and perpendicular radiation. Each table is generally similar to one of tables 152, having a correspondence between pixel identities P1, P2, . . . and intensity of radiation returning from the pixel. The intensities for table 352 are assumed to be A1, A2, A3, . . . ; the intensities for table 353 are assumed to be E1, E2, E3, . . . .

However, there is no requirement that only two types of polarized radiation are used in step 302, or that the types used have any special relation with the set of lines of the simulated wafer, and in general more than two types may be used. Thus, for linearly polarized radiation the directions of polarization may be selected to be substantially any of two or more directions relative to the set of lines being examined, and for elliptically polarized radiation the ellipticity may be set to be any values between 0 and 1.

Step 110 is generally as described for flowchart 100.

A step 304 replaces step 112. In step 304 signatures of blocks defined in step 110 are calculated as composite signatures formed from the intensity values in tables 352 and 353. For example, a block composite signature for a block comprising pixels P1, P2, P3 uses intensities A1, E1, A2, E2, A3, E3. In general a composite block signature CBSn is a function of the intensities from tables 352 and 353 for the pixels in block Bn.

In step 304 processor 36 forms a set of tables 354, typically under the direction of operator 31, each table having a one-to-one correspondence of a block identity and a composite signature. Tables 354 are generally similar to tables 154. By way of example, three tables 354A, 354B, and 354C are shown in FIG. 6, but in general the number of tables in the set of tables may be any convenient integer greater than or equal to two.

For any particular table 354, the expression used to form the composite block signatures of the table is typically a linear expression of the pixel intensities of tables 352 and 353. However, other expressions, such as a quadratic or other non-linear expression of the pixel intensities, may be used to form the composite block signatures.

Processor 36 implements steps 116, 122, and 118 generally as described above for flow chart 100. However, the correlation in step 118 is performed by correlating tables 354 with each reference table generated in step 102.

In addition, the tables formed in step 116 are formed by grouping the blocks of tables 354 according to the different axes used in reference wafer S28C. Thus in step 116 the blocks are grouped according to x-coordinates and according to y-coordinates, forming tables 356. Each table 354 is formed into one table having a one-to-one correspondences of x-coordinates and mean block signatures at the x-coordinates and a second table having a one-to-one correspondences of y-coordinates and mean block signatures at the y-coordinates. Thus table 354A generates an x-coordinate table 356XA and a y-coordinate table 356YA; table 354B generates an x-coordinate table 356XB and a y-coordinate table 356YB; and table 354C generates an x-coordinate table 356XC and a y-coordinate table 356YC.

A selection step 306 is generally similar to step 124 described above for flowchart 100. However, in flowchart 300 for step 306 processor 36 determines two optimal tables. A first optimal table 356XO, selected from tables 356XA, 356XB, . . . has a maximum sensitivity for the parameter of table 350X; a second optimal table 356YO, selected from tables 356YA, 356YB, . . . has a maximum sensitivity for the parameter of table 350Y. The processor stores the types of polarization used to generate optimal tables 356XO and 356YO in memory 38, and also stores the respective expressions, used in step 304, that form the optimal tables. In addition, the processor stores the block definition used to generate the optimal tables in the memory.

In some embodiments, prior to testing production wafers, processor 36 optimizes the types of polarization, the expressions, and the block definition stored in step 124 by testing on a physical calibration such as the FEM wafer described above with reference to flowchart 100. The optimization is performed in an optimization step 308, and values determined from the optimization step are stored in memory 38. The optional character of step 308 is indicated by broken lines in FIG. 5.

Processor 36 implements final step 126, generally as described for flowchart 100, on production wafers 28P using the values stored in memory 38. Since more than one type of polarization is stored, wafers 28P are scanned using all types of polarization that have been determined in step 306. The multiple scans at the respective different types of polarization are typically performed sequentially. In some embodiments, the multiple scans may be performed simultaneously, for example by using multiple simultaneous beams to irradiate surface 26.

From the results generated using the multiple scans, processor 36 uses the expressions stored in the memory to determine composite block signatures of the wafer, as described in step 304. Operator 31 uses the composite block signatures to estimate variations in the parameters-under-investigation across the production wafers 28P.

Flowchart 300 then ends.

Figure 8:
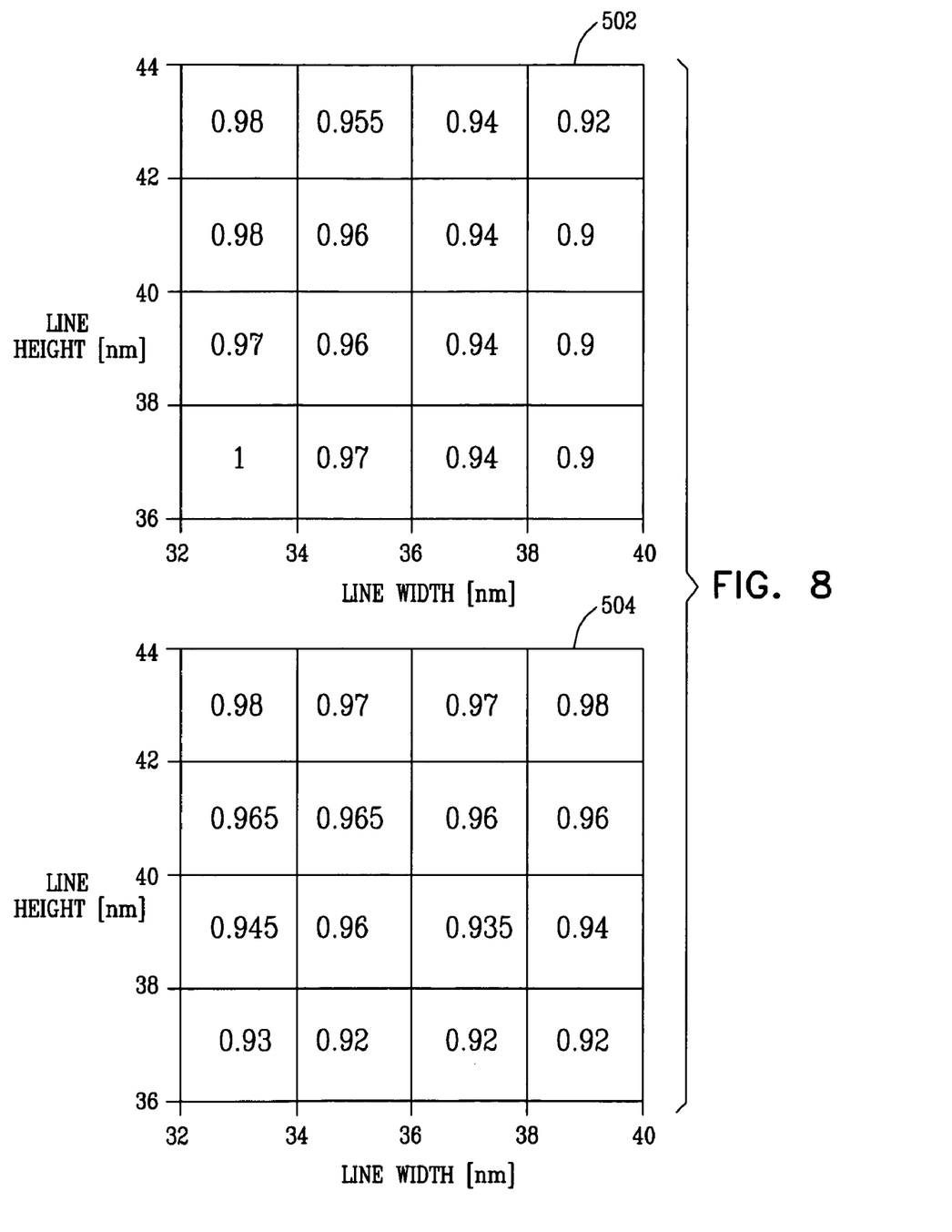
FIG. 8 shows exemplary results obtained using the process of the flowchart of FIG. 5, according to an embodiment of the present invention.

FIG. 8 shows exemplary results obtained using the process of flowchart 300, according to an embodiment of the present invention.

An optimal table 356XO was derived by using, in step 304, a first linear equation (1)

$$In = 3.5En - An \quad (1)$$

An optimal table 356Y0 was formed by using in step 304 a second linear equation (2):

$$In = En + 0.6An \quad (2)$$

In equations (1) and (2), n is a pixel identifier and In is a composite intensity generated by the pixel. The composite block signatures of step 304 are formed by summing values of In over all the pixels of a block.

Grid arrays 502 and 504 plot line height on a vertical axis and line width on a horizontal axis, the values corresponding to those of simulated wafer calibration wafer S28C (described above with reference to step 103 of flowchart 300).

Grid array 502 shows approximate values of composite block signatures, determined using optimal table 356XO, i.e., composite block signatures based on equation (1). Examination of the block signatures of grid array 502 shows that the composite block signatures have high sensitivity for changes of line width, and are substantially invariant with changes of line height. Thus equation (1) generates good composite pixel intensities and corresponding composite block signatures for examining varying line widths even in the presence of varying line heights.

Grid array 504 shows approximate values of composite block signatures, determined using optimal table 356YO, i.e., composite block signatures based on equation (2). Examination of the block signatures of grid array 504 shows that the composite block signatures have high sensitivity for changes of line height, and are substantially invariant with changes of line width. Thus equation (2) generates good composite pixel intensities and corresponding composite block signatures for examining varying line heights even in the presence of varying line widths.

Embodiments of the present invention replace the time-consuming measurements of systems such as SEMs with methods that are orders of magnitude faster than those of SEMs or comparable systems, and the inventors have found that the results from the two types of system are comparable. Because of their time consuming properties, systems such as SEMs or OCD measuring devices are typically only used on portions of a wafer. The faster operation of embodiments of the present invention means that a whole wafer can be measured in a relatively short time.

Embodiments of the present invention may be used in a wide range of applications wherein measurements of periodic structures are required. Some of the applications are itemized in pages 7 and 8 of U.S. Provisional Patent Application 60/950,077, incorporated herein.

Because of the relatively short time used by embodiments of the present invention, they may be applied in both feed-forward and feed-back systems. For example, examination of a present wafer may produce block signatures showing that line widths are close to a permissible range boundary, in which case feedback, such as processor 36 increasing or decreasing the intensity of radiation on a succeeding wafer, may be applied.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A method comprising:
   with a first measurement system having a first resolution, generating a reference calibration table of parameter variation that occurs on a surface of a sample object;
   dividing the surface of the sample object into pixels which are characterized by the parameter variation;
   defining blocks of the surface as respective groups of the pixels;
   with a second measurement system having a second resolution less than the first resolution (i) irradiating the pixels in multiple scans over the surface with radiation having different, respective types of polarization, and (ii) detecting returning radiation from the pixels in response to each of the scans;
   for each of the scans, (i) constructing respective block signatures of the blocks in response to the returning radiation from the group of pixels in each block, and (ii) determining a block signature variation using the respective block signatures of the blocks; and
   in response to a correlation between the block signature variation and the reference calibration table of parameter variation, the reference calibration table of parameter variation based on measurements at the first resolution and the block signature variation based on measurements at the second resolution less than the first resolution, selecting one of the types of polarization for use in subsequent examination of a test object.

2. The method according to claim 1, wherein the pixels tile the surface, and wherein the blocks comprise respective groups of contiguous pixels.

3. The method according to claim 1, wherein the types of polarization comprise at least two of a first linear polarization having a first polarization direction, a second linear polarization having a second polarization different from the first polarization direction, left circular polarization, right circular polarization, a first elliptical polarization, and a second elliptical polarization different from the first elliptical polarization, the first and second elliptical polarizations having an eccentricity between 0 and 1.

4. The method according to claim 1, wherein detecting the returning radiation comprises detecting at least one of bright field radiation, gray field radiation, and dark field radiation.

5. The method according to claim 1, wherein constructing the respective block signatures comprises defining a block signature function of respective intensities of the returning radiation from the pixels in a given block, and evaluating the block signature function for the blocks.

6. The method according to claim 5, wherein the block signature function comprises an arithmetic mean of the respective intensities.

7. The method according to claim 5, wherein examination of the test object comprises forming a test object block of test object pixels, and evaluating the block signature function for respective test object intensities of returning radiation from the test object pixels.

8. The method according to claim 1, wherein determining the block signature variation comprises determining a highest block signature variation, and wherein selecting one of the types of polarization comprises selecting a type of polarization for a scan having the highest block signature variation.

9. A method comprising:
with a first measurement system having a first resolution, generating a reference calibration table of parameter variation that occurs on a surface of a sample object;
dividing the surface of the sample object into pixels which are characterized by the parameter variation;
defining blocks of the surface as respective groups of the pixels;
with a second measurement system having a second resolution less than the first resolution (i) irradiating the pixels in multiple scans over the surface with radiation having different, respective types of polarization, and (ii) detecting returning radiation from the pixels in response to each of the scans;
constructing respective composite block signatures of the blocks in response to the returning radiation from the group of pixels in each block;
determining a composite block signature variation using the composite block signatures of the blocks; and
in response to a correlation between the composite block signature variation and the reference calibration table of parameter variation, the reference calibration table of parameter variation based on measurements at the first resolution and the composite block signature variation based on measurements at the second resolution less than the first resolution, selecting two or more of the types of polarization for use in subsequent examination of a test object.

10. The method according to claim 9, wherein constructing the respective composite block signatures comprises defining a composite block signature function of intensities of the returning radiation from at least two of the multiple scans and from the pixels in a given block, and evaluating the composite block signature function for the blocks.

11. The method according to claim 10, wherein examination of the test object comprises forming a test object block of test object pixels, and evaluating the composite block signature function for respective test object intensities of returning radiation from the test object pixels.

12. The method according to claim 9, wherein determining the composite block signature variation comprises determining a highest composite block signature variation, and wherein selecting the two or more types of polarization comprises selecting types of polarization corresponding to scans forming a highest composite block signature variation.

13. An apparatus comprising:
a processor configured to:
generate a reference calibration table of parameter variation that occurs on a surface of a sample object based on measurements at a first resolution;
divide the surface of the sample object into pixels which are characterized by the parameter variation, and
define blocks of the surface as respective groups of the pixels; and
a radiation scanner having a second resolution less than the first resolution configured to:
irradiate the pixels in multiple scans over the surface with radiation having different, respective types of polarization, and
detect returning radiation from the pixels in response to each of the scans,
wherein the processor is further configured to:
for each of the scans, (i) construct respective block signatures of the blocks in response to the returning radiation from the group of pixels in each block, and (ii) determine a block signature variation using the block signatures of the blocks, and
in response to a correlation between the block signature variation and the reference calibration table of parameter variation, the reference calibration table of parameter variation based on measurements at the first resolution and the block signature variation based on measurements at the second resolution less than the first resolution, select one of the types of polarization for use in subsequent examination of a test object.

14. An apparatus comprising:
a processor configured to:
generate a reference calibration table of parameter variation that occurs on a surface of a sample object based on measurements at a first resolution;
divide the surface of the sample object into pixels which are characterized by the parameter variation, and
define blocks of the surface as respective groups of the pixels; and
a radiation scanner having a second resolution less than the first resolution configured to:
irradiate the pixels in multiple scans over the surface with radiation having different, respective types of polarization, and
detect returning radiation from the pixels in response to each of the scans,
wherein the processor is further configured to:
construct respective composite block signatures of the blocks in response to the returning radiation from the group of pixels in each block,
determine a composite block signature variation using the composite block signatures of the blocks, and
in response to a correlation between the composite block signature variation and the reference calibration table of parameter variation, the reference calibration table of parameter variation based on measurements at the first resolution and the composite block signature variation based on measurements at the second resolution less than the first resolution, select two or more of the types of polarization for use in subsequent examination of a test object.

15. A method comprising:
generating a reference calibration table of parameter variation that occurs on a surface of a sample object based on simulated measurements at a first resolution;
simulating the surface of the sample object as a simulated surface, and defining simulated characteristics of the simulated surface;

dividing the simulated surface into pixels which are characterized by the parameter variation;

defining blocks of the simulated surface as respective groups of the pixels;

at a second resolution less than the first resolution, (i) simulating irradiation of the pixels in multiple scans over the simulated surface with radiation having different, respective types of polarization, and (ii) simulating detection of returning radiation from the pixels in response to each of the scans;

for each of the scans, (i) constructing respective block signatures of the blocks in response to the returning radiation from the group of pixels in each block, and (ii) determining a block signature variation using the block signatures of the blocks; and in response to a correlation between the block signature variation and the reference calibration table of parameter variation, the reference calibration table of parameter variation based on measurements at the first resolution and the block signature variation based on measurements at the second resolution less than the first resolution, selecting one of the types of polarization for use in subsequent physical examination of a test object.

16. The method according to claim 15, wherein determining the block signature variation comprises determining a highest block signature variation, and wherein selecting one of the types of polarization comprises selecting a type of polarization for a scan having a highest block signature variation.

17. A method comprising:

generating a reference calibration table of parameter variation that occurs on a surface of a sample object based on simulated measurements at a first resolution;

simulating the surface of the sample object as a simulated surface, and defining simulated characteristics of the simulated surface;

dividing the simulated surface into pixels which are characterized by the parameter variation;

defining blocks of the simulated surface as respective groups of the pixels;

at second resolution less than the first resolution, (i) simulating irradiation of the pixels in multiple scans over the simulated surface with radiation having different, respective types of polarization, and (ii) simulating detection of returning radiation from the pixels in response to each of the scans;

constructing respective composite block signatures of the blocks in response to the returning radiation from the group of pixels in each block;

determining a composite block signature variation using the composite block signatures of the blocks; and in response to a correlation between the composite block signature variation and the reference calibration table of parameter variation, the reference calibration table of parameter variation based on measurements at the first resolution and the composite block signature variation based on measurements at the second resolution less than the first resolution, selecting two or more of the types of polarization for use in subsequent physical examination of a test object.

18. The method according to claim 17, wherein determining the block signature variation comprises determining a highest composite block signature variation, and wherein selecting the two or more types of polarization comprises selecting types of polarization corresponding to scans forming a highest composite block signature variation.

19. A method comprising:

dividing a surface of a sample object into pixels which are characterized by a non-varying parameter;

defining blocks of the surface as respective groups of the pixels;

irradiating the pixels in multiple scans over the surface with radiation having different, respective types of polarization;

detecting returning radiation from the pixels in response to each of the scans;

for each of the scans, (i) constructing respective block signatures of the blocks in response to the returning radiation from the group of pixels in each block, (ii) determining a block signature variation using the block signatures of the blocks; and (iii) forming a correlation coefficient between the block signatures of the blocks and the non-varying parameter;

in response to the block signature variation, selecting a type of polarization for a scan having a highest correlation coefficient for use in subsequent inspection of a test object.

* * * * *